(12) United States Patent
Chekler et al.

(10) Patent No.: US 9,920,043 B2
(45) Date of Patent: Mar. 20, 2018

(54) CRYSTALLINE FORM OF 6-[(4R)-4-METHYL-1,2-DIOXIDO-1,2,6-THIADIAZINAN-2-YL]IOSOQUINOLINE-1-CARBONITRILE

(71) Applicant: Pfizer Inc., New York, NY (US)

(72) Inventors: Eugene Lvovich Piatnitski Chekler, Concord, MA (US); Roberta Louise Dorow, Kalamazoo, MI (US); Jeffrey Braden Sperry, East Lyme, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/310,570

(22) PCT Filed: May 1, 2015

(86) PCT No.: PCT/IB2015/053194
§ 371 (c)(1),
(2) Date: Nov. 11, 2016

(87) PCT Pub. No.: WO2015/173684
PCT Pub. Date: Nov. 19, 2015

(65) Prior Publication Data
US 2017/0073338 A1   Mar. 16, 2017

Related U.S. Application Data

(60) Provisional application No. 62/138,037, filed on Mar. 25, 2015, provisional application No. 61/993,693, filed on May 15, 2014.

(51) Int. Cl.
*C07D 471/04* (2006.01)
*C07D 417/04* (2006.01)
*A61K 9/00* (2006.01)
*A61K 31/549* (2006.01)

(52) U.S. Cl.
CPC .......... *C07D 417/04* (2013.01); *A61K 9/0053* (2013.01); *A61K 31/549* (2013.01)

(58) Field of Classification Search
CPC .................................................. C07D 471/04
See application file for complete search history.

(56) References Cited

U.S. PATENT DOCUMENTS 6,106,864 A   8/2000 Dolan et al.

FOREIGN PATENT DOCUMENTS

| WO | 91/11172 A1 | 8/1991 |
| WO | 94/02518 A1 | 2/1994 |
| WO | 98/55148 A1 | 12/1998 |
| WO | 00/35298 A1 | 6/2000 |
| WO | 2004/110978 A2 | 12/2004 |
| WO | 2005/018573 A2 | 3/2005 |
| WO | 2009/082437 A2 | 7/2009 |
| WO | 2014/087298 A1 | 6/2014 |

OTHER PUBLICATIONS

Liang et al, "Fast-dissolving intraoral drug delivery systems", Expert Opinion in Therapeutic Patents 11(6):981-986 (2001).
Verma et al, "Current Status of Drug Delivery Technologies and Future Directions", Pharmaceutical Technology On-Line 25(2)1-14 (2001).

*Primary Examiner* — Bruck Kifle
(74) *Attorney, Agent, or Firm* — John A. Wichtowski (57) ABSTRACT

This invention relates to a novel crystalline form of 6-[(4R)-4-methyl-1,1-dioxido-1,2,6-thiadiazinan-2-yl]isoquinoline-1-carbonitrile which is useful as a selective androgen receptor modulator (SARM), and to compositions thereof and suitable processes for the preparation thereof.

3 Claims, 4 Drawing Sheets

CRYSTALLINE FORM OF 6-[(4R)-4-METHYL-1,2-DIOXIDO-1,2,6-THIADIAZINAN-2-YL]IOSOQUINOLINE-1-CARBONITRILE

FIELD OF THE INVENTION

The present invention relates to a crystalline form of 6-[(4R)-4-methyl-1,1-dioxido-1,2,6-thiadiazinan-2-yl]isoquinoline-1-carbonitrile, compositions thereof and to processes for the preparation thereof. The invention also relates to a crystalline form of 6-[(4R)-4-methyl-1,1-dioxido-1,2,6-thiadiazinan-2-yl]isoquinoline-1-carbonitrile for the treatment of diseases and disorders that are related to the modulation of the androgen receptor.

BACKGROUND

The androgen receptor ("AR") is a ligand-activated transcriptional regulatory protein that mediates induction of male sexual development and function through its activity with endogenous androgens. Androgenic steroids play an important role in many physiologic processes, including the development and maintenance of male sexual characteristics such as muscle and bone mass, prostate growth, spermatogenesis, and the male hair pattern. The endogenous steroidal androgens include testosterone and dihydrotestosterone ("DHT"). Steroidal ligands which bind the AR and act as androgens (e.g. testosterone enanthate) or as antiandrogens (e.g. cyproterone acetate) have been known for many years and are used clinically.

6-[(4R)-4-Methyl-1,1-dioxido-1,2,6-thiadiazinan-2-yl] isoquinoline-1-carbonitrile (Formula I), in its free base form, has the chemical formula $C_{14}H_{14}N_4SO_2$ and the following structural formula:

Formula I

Synthesis of 6-[(4R)-4-methyl-1,1-dioxido-1,2,6-thiadiazinan-2-yl]isoquinoline-1-carbonitrile is disclosed in copending international patent application, PCT/IB2013/060381, filed 25 Nov. 2013, and published as WO 2014/087298 on 12 Jun. 2014, assigned to the assignee of the present invention and which is incorporated herein by reference in its entirety. 6-[(4R)-4-Methyl-1,1-dioxido-1,2,6-thiadiazinan-2-yl]isoquinoline-1-carbonitrile is known to be active as a selective androgen receptor modulator (SARM) and, as such, is useful for treating and/or preventing a variety of hormone-related conditions, for example, conditions associated with androgen decline, such as, inter alia, anaemia; anorexia; arthritis; bone disease; musculoskeletal impairment; cachexia; frailty; age-related functional decline in the elderly; growth hormone deficiency; hematopoietic disorders; hormone replacement; loss of muscle strength and/or function; muscular dystrophies; muscle loss following surgery; muscular atrophy; neurodegenerative disease; neuromuscular disease; obesity; osteoporosis; and, muscle wasting.

Identification of new solid forms of a known pharmaceutical active ingredient provide a means of optimising either the physicochemical, stability, manufacturability and/or bioperformance characteristics of the active pharmaceutical ingredient without modifying its chemical structure. Based on a chemical structure, one cannot predict with any degree of certainty whether a compound will crystallise, under what conditions it will crystallise, or the solid state structure of any of those crystalline forms. The specific solid form chosen for drug development can have dramatic influence on the properties of the drug product. The selection of a suitable solid form is partially dictated by yield, rate and quantity of the crystalline structure. In addition, hygroscopicity, stability, solubility and the process profile of the solid form such as compressibility, powder flow and density are important considerations.

As such, there is a need to identify solid forms of 6-[(4R)-4-methyl-1,1-dioxido-1,2,6-thiadiazinan-2-yl]isoquinoline-1-carbonitrile that exhibit acceptable physicochemical, stability, manufacturability and/or bioperformance properties.

SUMMARY OF THE INVENTION

This invention relates to a crystalline form of 6-[(4R)-4-methyl-1,1-dioxido-1,2,6-thiadiazinan-2-yl]isoquinoline-1-carbonitrile.

In another aspect, this invention relates to a pharmaceutical composition comprising a crystalline form of 6-[(4R)-4-methyl-1,1-dioxido-1,2,6-thiadiazinan-2-yl]isoquinoline-1-carbonitrile and a pharmaceutical carrier or excipient.

In another aspect, this invention relates to a method for modulating an activity of an androgen receptor in a subject in need thereof, comprising contacting said androgen receptor with an effective amount of a crystalline form of 6-[(4R)-4-methyl-1,1-dioxido-1,2,6-thiadiazinan-2-yl]isoquinoline-1-carbonitrile, or a pharmaceutical composition thereof, thereby modulating the activity of said androgen receptor.

In yet another aspect, this invention relates to a method for treating a disorder or condition in a subject, wherein the disorder or condition is selected from among anemia; anorexia; arthritis; bone disease; musculoskeletal impairment; cachexia; frailty; age-related functional decline in the elderly; growth hormone deficiency; hematopoietic disorders; hormone replacement; hypogonadism; loss of muscle strength and/or function; muscular dystrophies; muscle loss following surgery; muscular atrophy; neurodegenerative disease; neuromuscular disease; obesity; osteoporosis; sarcopenia, including sarcopenia in chronic obstructive pulmonary disease; and, muscle wasting comprising administering to said subject an effective amount of a crystalline form of 6-[(4R)-4-methyl-1,1-dioxido-1,2,6-thiadiazinan-2-yl]isoquinoline-1-carbonitrile, or a pharmaceutical composition thereof, thereby treating said disease or condition.

In a further aspect, this invention relates to a process for preparing a crystalline form of 6-[(4R)-4-methyl-1,1-dioxido-1,2,6-thiadiazinan-2-yl]isoquinoline-1-carbonitrile.

In particular, the crystalline form of the present invention has been shown to have suitable physicochemical, stability, manufacturability and/or bioperformance properties which render it useful for further development.

DETAILED DESCRIPTION OF THE INVENTION

This invention relates to a crystalline form of 6-[(4R)-4-methyl-1,1-dioxido-1,2,6-thiadiazinan-2-yl]isoquinoline-1-carbonitrile.

According to the present invention, 6-[(4R)-4-methyl-1,1-dioxido-1,2,6-thiadiazinan-2-yl]isoquinoline-1-carbonitrile is in its free base form.

In another embodiment, the present invention relates to a crystalline form of 6-[(4R)-4-methyl-1,1-dioxido-1,2,6-thiadiazinan-2-yl]isoquinoline-1-carbonitrile which is Form (1).

There are a number of analytical methods one of ordinary skill in the art can use to analyze solid forms, in particular crystalline solid forms. The term "analyze" as used herein shall be taken to mean to obtain information about the solid state structure of solid forms. For example, X-ray powder diffraction is one such suitable technique for differentiating amorphous solid forms from crystalline solid forms and for characterizing and identifying crystalline solid forms since different crystalline forms exhibit different X-ray powder patterns. A discussion of the theory of X-ray powder diffraction patterns can be found in Clearfield, Reibenspies and Bhuvanesh (Editors), Principles and Applications of Powder Diffraction: Edition 1, Wiley, John & Sons, Incorporated (2008), which is incorporated by reference in its entirety.

Due to differences in instruments, samples and sample preparation, minor variation in peak values in spectroscopic techniques can occur. In an X-ray powder diffraction pattern typical precision of a 2-theta x-axis value of an x-ray powder pattern is of the order of plus or minus 0.2° 2-theta. As such, a peak value reported to be at 9.2° 2-theta could occur at anywhere between 9.0° 2-theta and 9.4° 2-theta when measured on most x-ray diffractometers under most conditions. In a FT-Raman spectra typical precision of a Raman shift is of the order of plus or minus 2 cm$^{-1}$. In a solid state NMR the typical precision of a $^{13}$C peak shift is of the order of plus or minus 0.2 ppm.

In a further preferred embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9 and 15.2.

In a yet further preferred embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9, and 15.2 and one or more additional characteristic peaks expressed in degrees 2-theta (±0.2° 2-theta) selected from the group consisting of 17.1, 17.3, and 18.5.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9, 15.2 and 17.1.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9, 15.2 and 17.3.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9, 15.2 and 18.5.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9, 15.2, 17.1 and 17.3.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9, 15.2 17.1, and 18.5.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9, 15.2 17.3, and 18.5.

In a still further preferred embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9, 15.2, 17.1, 17.3, and 18.5.

In an even further preferred embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) as depicted in Table 1.

In another embodiment of the present invention, the crystalline form of 6-[(4R)-4-methyl-1,1-dioxido-1,2,6-thiadiazinan-2-yl]isoquinoline-1-carbonitrile Form (1) exhibits a FT-Raman spectra having characteristic peaks expressed in cm$^{-1}$ (±2 cm$^{-1}$) at 708, 1555 and 2230.

In another embodiment of the present invention, the crystalline form of 6-[(4R)-4-methyl-1,1-dioxido-1,2,6-thiadiazinan-2-yl]isoquinoline-1-carbonitrile Form (1) exhibits a FT-Raman spectra having characteristic peaks expressed in cm$^{-1}$ (±2 cm$^{-1}$) as depicted in Table 2.

In another embodiment of the present invention, the crystalline form of 6-[(4R)-4-methyl-1,1-dioxido-1,2,6-thiadiazinan-2-yl]isoquinoline-1-carbonitrile Form (1) exhibits a solid state NMR spectra having characteristic peaks expressed in ppm (±0.2 ppm) at 15.3 and 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits a solid state NMR spectra having characteristic peaks expressed in ppm (±0.2 ppm) at 15.3, 136.6 and 143.2.

In another embodiment of the present invention, the crystalline form of 6-[(4R)-4-methyl-1,1-dioxido-1,2,6-thiadiazinan-2-yl]isoquinoline-1-carbonitrile Form (1) exhibits a solid state NMR spectra having characteristic peaks expressed in ppm (±0.2 ppm) as depicted in Table 3.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8 and 10.9 and exhibits a FT-Raman spectra having one or more characteristic peaks expressed in $cm^{-1}$ (±2 $cm^{-1}$) selected from the group consisting of 708, 1555 and 2230.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8 and 10.9 and exhibits a FT-Raman spectra having a characteristic peak expressed in $cm^{-1}$ (±2 $cm^{-1}$) at 708.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9 and 15.2 and exhibits a FT-Raman spectra having characteristic peaks expressed in $cm^{-1}$ (±2 $cm^{-1}$) at 708, 1555 and 2230.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8 and 10.9 and exhibits a solid state NMR spectra having a characteristic peak expressed in ppm (±0.2 ppm) at 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9 and 15.2 and exhibits a solid state NMR spectra having a characteristic peak expressed in ppm (±0.2 ppm) at 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9 and 15.2 and exhibits a solid state NMR spectra having characteristic peaks expressed in ppm (±0.2 ppm) at 15.3 and 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits a FT-Raman spectra having characteristic peaks expressed in $cm^{-1}$ (±2 $cm^{-1}$) at 708 and 2230 and exhibits a solid state NMR spectra having a characteristic peak expressed in ppm (±0.2 ppm) at 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits a FT-Raman spectra having characteristic peaks expressed in $cm^{-1}$ (±2 $cm^{-1}$) at 708 and 2230 and exhibits a solid state NMR spectra having characteristic peaks expressed in ppm (±0.2 ppm) at 15.3 and 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits a FT-Raman spectra having characteristic peaks expressed in $cm^{-1}$ (±2 $cm^{-1}$) at 708, 1555 and 2230 and exhibits a solid state NMR spectra having characteristic peaks expressed in ppm (±0.2 ppm) at 15.3 and 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8 and 10.9, a FT-Raman spectra having characteristic peaks expressed in $cm^{-1}$ (±2 $cm^{-1}$) at 708 and 2230 and exhibits a solid state NMR spectra having a characteristic peak expressed in ppm (±0.2 ppm) at 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8 and 10.9, a FT-Raman spectra having characteristic peaks expressed in $cm^{-1}$ (±2 $cm^{-1}$) at 708 and 2230 and exhibits a solid state NMR spectra having characteristic peaks expressed in ppm (±0.2 ppm) at 15.3 and 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9 and 15.2, a FT-Raman spectra having characteristic peaks expressed in $cm^{-1}$ (±2 $cm^{-1}$) at 708, 1555 and 2230 and exhibits a solid state NMR spectra having characteristic peaks expressed in ppm (±0.2 ppm) at 15.3 and 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8 and 10.9 and exhibits either a FT-Raman spectra having one or more characteristic peaks expressed in $cm^{-1}$ (±2 $cm^{-1}$) selected from the group consisting of 708, 1555 and 2230; and/or a solid state NMR spectra having a characteristic peak expressed in ppm (±0.2 ppm) at 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits a FT-Raman spectra having characteristic peaks expressed in $cm^{-1}$ (±2 $cm^{-1}$) at 708 and 2230 and exhibits either an X-ray powder diffraction pattern having one or more characteristic peaks expressed in degrees 2-theta (±0.2° 2-theta) selected from the group consisting of 7.8, 10.9, 15.2, 17.1, 17.3, and 18.5; and/or a solid state NMR spectra having a characteristic peak expressed in ppm (±0.2 ppm) at 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits a solid state NMR spectra having a characteristic peak expressed in ppm (±0.2 ppm) at 136.6 and exhibits either an X-ray powder diffraction pattern having one or more characteristic peaks expressed in degrees 2-theta (±0.2° 2-theta) selected from the group consisting of 7.8, 10.9, 15.2, 17.1, 17.3, and 18.5; and/or exhibits a FT-Raman spectra having one or more characteristic peaks expressed in cm$^{-1}$ (±2 cm$^{-1}$) selected from the group consisting of 708, 1555 and 2230.

In a preferred embodiment of the present invention, the crystalline form of 6-[(4R)-4-methyl-1,1-dioxido-1,2,6-thiadiazinan-2-yl]isoquinoline-1-carbonitrile is anhydrous.

In another embodiment of the present invention, the crystalline form of 6-[(4R)-4-methyl-1,1-dioxido-1,2,6-thiadiazinan-2-yl]isoquinoline-1-carbonitrile Form (1) is anhydrous.

As used herein the term "anhydrous" shall be taken to mean that the crystalline form contains less than about 5% w/w, more preferably less than about 1% w/w and even more preferably less than about 0.5% w/w of the solvent of crystallisation or water. In another embodiment the term "anhydrous" shall be taken to mean that the crystalline form contains less than about 1% w/w of the solvent of crystallisation or water.

The crystalline form of 6-[(4R)-4-methyl-1,1-dioxido-1,2,6-thiadiazinan-2-yl]isoquinoline-1-carbonitrile, including crystalline 6-[(4R)-4-methyl-1,1-dioxido-1,2,6-thiadiazinan-2-yl]isoquinoline-1-carbonitrile Form (1), can be prepared from commercially available starting materials, compounds known in the literature, or readily prepared intermediates by employing the general reaction schemes provided herein in conjunction with standard synthetic methods and procedures known to those skilled in the art. Standard synthetic methods and procedures for the preparation of organic molecules and functional group transformations and manipulations can be readily obtained from the relevant scientific literature or from standard text books in the field. It will be appreciated that where typical or preferred process conditions are stated (i.e. reaction temperatures, times mole rations or reactants, solvents, pressures etc.), one of ordinary skill may substitute these with alternative process conditions unless otherwise stated. Optimum reaction conditions can vary with the particular reactants or solvent used. Those skilled in the art will recognize that the nature and order of the synthetic steps presented can be varied for the purpose of optimizing the formation of the compounds described herein.

The general reaction schemes provided herein illustrate the preparation of 6-[(4R)-4-methyl-1,1-dioxido-1,2,6-thiadiazinan-2-yl]isoquinoline-1-carbonitrile (Formula I).

The starting material bromide is coupled with an aminoalcohol II under coupling conditions such as Pd-catalyzed coupling conditions. The hydroxyl group of compound III is activated as a leaving group by mesylate formation among other methods in the presence of a base to generate compound IV. The treatment of compound IV with the reagent V produces Boc-protected intermediates VI. Boc-group de-protection followed by alkylation or acylating of intermediate NH compounds culminates the synthesis forming the compound of Formula I.

A crystalline form of 6-[(4R)-4-methyl-1,1-dioxido-1,2,6-thiadiazinan-2-yl]isoquinoline-1-carbonitrile, including Form (1), can then be prepared by crystallization of the compound of Formula I from a solvent, preferably a solvent comprising acetone or, in an alternative embodiment, from a solvent comprising acetone and water. In one embodiment the solvent is acetone. In another embodiment the solvent is acetone and water. The crystalline form so prepared can be further dried, preferably under vacuum, to form the anhydrous form.

Accordingly, this invention also relates to a process for preparing a crystalline form of 6-[(4R)-4-methyl-1,1-dioxido-1,2,6-thiadiazinan-2-yl]isoquinoline-1-carbonitrile, which process comprises the step of crystallization of 6-[(4R)-4-methyl-1,1-dioxido-1,2,6-thiadiazinan-2-yl]isoquinoline-1-carbonitrile from a solvent, wherein the solvent preferably comprises acetone. In an alternative embodiment, the solvent comprises acetone and water.

Accordingly, this invention also relates to a process for preparing crystalline 6-[(4R)-4-methyl-1,1-dioxido-1,2,6-thiadiazinan-2-yl]isoquinoline-1-carbonitrile Form (1), which process comprises the step of crystallization of 6-[(4R)-4-methyl-1,1-dioxido-1,2,6-thiadiazinan-2-yl]isoquinoline-1-carbonitrile from a solvent, wherein the solvent preferably comprises acetone. In an alternative embodiment, the solvent comprises acetone and water.

The present invention also relates to a pharmaceutical composition comprising a crystalline form of 6-[(4R)-4-methyl-1,1-dioxido-1,2,6-thiadiazinan-2-yl]isoquinoline-1-carbonitrile and a pharmaceutically acceptable carrier or excipient, and to methods for preparing such pharmaceutical compositions.

In another embodiment, the present invention also relates to a pharmaceutical composition comprising crystalline 6-[(4R)-4-methyl-1,1-dioxido-1,2,6-thiadiazinan-2-yl]isoquinoline-1-carbonitrile Form (1) and a pharmaceutically acceptable carrier or excipient, and to methods for preparing such pharmaceutical compositions.

As used herein the term "excipient" is taken to mean any ingredient in the pharmaceutical composition other than the crystalline form of 6-[(4R)-4-methyl-1,1-dioxido-1,2,6-thiadiazinan-2-yl]isoquinoline-1-carbonitrile. The choice of excipient will depend to a large extent on factors such as the particular mode of administration, the effect of the excipient on solubility and stability, and the nature of the dosage form, which factors are well known to the person skilled in the art. The term "excipient" encompasses diluent, carrier or adjuvant.

Pharmaceutical compositions suitable for the delivery of a crystalline form of 6-[(4R)-4-methyl-1,1-dioxido-1,2,6-thiadiazinan-2-yl]isoquinoline-1-carbonitrile and methods for their preparation can be readily determined by one skilled in the art. Such compositions and methods for preparation may be found, for example, in Remington's Pharmaceutical Sciences, 19$^{th}$ Edition (Mack Publishing Company, 1995).

Preferred pharmaceutical compositions of the present invention are those suitable for oral administration. Oral administration may involve swallowing, so that the pharmaceutically active ingredient enters the gastrointestinal tract, or alternatively, oral administration may involve buccal or sublingual administration by which the pharmaceutically active ingredient enters the blood stream directly from the mouth. Formulations suitable for oral administration include solid formulations such as tablets, capsules containing particulates, liquids, or powders, lozenges (including liquid filled), chews, multi- and nano-particulates, gels, solid solution, liposomes, films, ovules, sprays and liquid formulations.

Tablet formulations suitable for oral administration usually comprise from about 0.1% w/w to about 80% w/w of the active pharmaceutical ingredient, dependent on dose, more typically from 5% w/w to about 60% w/w of the dosage form. One of ordinary skill will appreciate that one of the factors to consider when determining the level of active pharmaceutical ingredient suitable for inclusion in a tablet for oral administration is that needed to ensure adequate patient dosing. For example, when dealing with an active ingredient which is potent or highly potent, tablet formulations suitable for oral administration may comprise a lower amount of active pharmaceutical ingredient, for example from about 0.1% w/w to about 20% w/w of the active pharmaceutical ingredient.

In addition to the active pharmaceutical ingredient, tablets suitable for oral administration also comprise one or more of the following excipients. Tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from about 1% w/w to about 25% w/w. In one embodiment of the present invention, the disintegrant will comprise from about 5% w/w to about 20% w/w of the dosage form. Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate. Tablets may also optionally comprise surface active agents, such as sodium lauryl sulfate and polysorbate 80, and glidants such as silicon dioxide and talc. When present, surface active agents may comprise from about 0.2% w/w to about 5% w/w of the tablet, and glidants may comprise from about 0.2% w/w to about 1% w/w of the tablet. Tablets also generally contain lubricants such as magnesium stearate, calcium stearate, zinc stearate, sodium stearyl fumarate, and mixtures of magnesium stearate with sodium lauryl sulfate. Lubricants generally comprise from about 0.25% w/w to about 10% w/w. In one embodiment of the present invention, lubricants comprise from about 0.5% w/w to about 3% w/w of the tablet. Other possible ingredients include anti-oxidants, colorants, flavoring agents, preservatives and taste-masking agents.

For example, exemplary tablet formulations comprise up to about 80% w/w of the active pharmaceutical ingredient, from about 0% w/w to about 90% w/w binder, from about 0% w/w to about 95% w/w diluent, from about 1% w/w to about 25% w/w disintegrant, and from about 0.25% w/w to about 10% w/w lubricant.

Tablet blends may be compressed directly or by roller to form tablets. Tablet blends, or portions of blends, may alternatively be wet-, dry-, or melt-granulated, melt congealed, or extruded before tableting. The final formulation may comprise one or more layers, and may be coated or uncoated; it may even be encapsulated. Formulations of tablets are discussed in Pharmaceutical Dosage Forms: Tablets, Vol. 1, by H. Lieberman and L. Lachman (Marcel Dekker, New York, 1980).

When preparing pharmaceutical compositions of the present invention, it may be necessary to adjust the particle volume mean diameter and/or the particle size distribution of the crystalline active pharmaceutical ingredient to further optimise its physicochemical properties or other properties such as stability manufacturability and/or bioperformance. For example, in some cases there may be a desire to reduce the particle size to increase the rate of dissolution. Particle size reduction is also sometimes used to ensure content uniformity for formulations which have very low loading of active pharmaceutical ingredients. For the present invention it is preferred that the crystalline form of the active pharmaceutical ingredient has a volume mean diameter of no more than 50 µm and a particle size distribution such that 95% of the sample volume particles have a diameter of no more than 130 µm, as measured by laser diffraction, with dry dispersion, using standard techniques.

Formulations suitable for oral administration also include fast-dissolving or fast-disintegrating dose forms such as those described in Expert Opinion in Therapeutic Patents, 11(6), 981-986 by Lang and Chen (2001).

Solid formulations for oral administration may be formulated to be immediate and/or modified release. Modified release includes delayed, sustained, pulsed, controlled, targeted and programmed release. Suitable modified release formulations for the purposes of the invention are described in U.S. Pat. No. 6,106,864. Details of other suitable release technologies such as high energy dispersions and osmotic and coated particles are to be found in Pharmaceutical Technology On-line, 25(2), 1-14, by Verma et al. (2001). The use of chewing gum to achieve controlled release is described in WO-A-00/35298.

Other pharmaceutical compositions of the present invention suitable for oral administration include consumable oral films. These are typically pliable water-soluble or water-swellable thin film dosage forms which may be rapidly dissolving or mucoadhesive and typically comprise a film-forming polymer, a binder, a solvent, a humectant, a plasticizer, a stabilizer or emulsifier, a viscosity-modifying agent and a solvent. Some components of the formulation may perform more than one function. The film-forming polymer may be selected from natural polysaccharides, proteins, or synthetic hydrocolloids and, when included in a composition, the film-forming polymer is typically present in the range of about 0.01% w/w to about 99% w/w, more typically in the range of about 30% w/w to about 80% w/w. Other possible ingredients include anti-oxidants, colorants, flavorings and flavor enhancers, preservatives, salivary stimulating agents, cooling agents, co-solvents (including oils), emollients, bulking agents, anti-foaming agents, surfactants and taste-masking agents. Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Other suitable pharmaceutical compositions of the present invention also include liquid formulations. Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Pharmaceutical compositions of the present invention may also be adapted for administration of the active directly into the blood stream, into muscle, or into an internal organ. Such parenteral administration includes intravenous, intraarterial, intraperitoneal, intrathecal, intraventricular, intraurethral, intrasternal, intracranial, intramuscular and subcutaneous administration. Suitable devices for parenteral administration include needle (including microneedle) injectors, needle-free injectors and infusion techniques. Suitable pharmaceutical compositions also include those for topical administration to the skin or mucosa, that is, dermally or transdermally.

Yet another suitable pharmaceutical composition of the present invention are those adapted for intranasal administration or for inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin. The pressurized container, pump, spray, atomizer, or nebulizer contains a solution or suspension of the pharmaceutically active ingredient, which solution or suspension also comprises for example, ethanol, aqueous ethanol, or a suitable alternative agent for dispersing, solubilizing, or extending release of the compound, a propellant as solvent and an optional surfactant, such as sorbitan trioleate, oleic acid, or an oligolactic acid. Prior to use in a dry powder or suspension formulation, the drug product is micronized to a size suitable for delivery by inhalation (typically less than 5 µm). This may be achieved by any appropriate comminuting method, such as spiral jet milling, fluid bed jet milling, supercritical fluid processing to form nanoparticles, high pressure homogenization, or spray drying. Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose. Formulations for intranasal administration may be formulated to be immediate and/or modified release using, for example, PGLA. Modified release includes delayed, sustained, pulsed, controlled, targeted and programmed release.

Pharmaceutical compositions of the present invention also include those formulated to be administered directly to the eye or ear, typically in the form of drops of a micronized suspension or solution in isotonic, pH-adjusted, sterile saline.

Pharmaceutical compositions of the present invention optionally comprise flavors. Suitable flavors, such as menthol and levomenthol, or sweeteners, such as saccharin or saccharin sodium, may be added.

Pharmaceutical compositions of the present invention optionally also comprise soluble macromolecular entities, such as cyclodextrin and suitable derivatives thereof or polyethylene glycol-containing polymers, in order to improve the solubility, dissolution rate, taste, bioavailability and/or stability of the active ingredient when using any of the aforementioned modes of administration. Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e., as a carrier, diluent, or solubilizer. Most commonly used for these purposes are alpha-, beta- and gamma-cyclodextrins, examples of which may be found in international patent publications WO-A-91/11172, WO-A-94/02518 and WO-A-98/55148.

Preferred pharmaceutical compositions of the present invention are those which are suitable for oral administration. More preferably pharmaceutical compositions of the present invention are suitable for oral administration and are in the form of a tablet or a capsule.

In another aspect this invention relates to a method for modulating an activity of an androgen receptor in a subject in need thereof, comprising contacting said androgen receptor with an effective amount of a crystalline form of 6-[(4R)-4-methyl-1,1-dioxido-1,2,6-thiadiazinan-2-yl]isoquinoline-1-carbonitrile, or a pharmaceutical composition thereof, thereby modulating the activity of said androgen receptor.

In another aspect this invention relates to a method for modulating an activity of an androgen receptor in a subject in need thereof, comprising contacting said androgen receptor with an effective amount of crystalline 6-[(4R)-4-methyl-1,1-dioxido-1,2,6-thiadiazinan-2-yl]isoquinoline-1-carbonitrile Form (1), or a pharmaceutical composition thereof, thereby modulating the activity of said androgen receptor.

This invention also relates to a method of treating a disorder or condition relating to dysregulation of an androgen receptor in a subject, comprising administering to the subject a therapeutically effective amount of a crystalline form of 6-[(4R)-4-methyl-1,1-dioxido-1,2,6-thiadiazinan-2-yl]isoquinoline-1-carbonitrile, or a pharmaceutical composition thereof.

This invention also relates to a method of treating a disorder or condition relating to dysregulation of an androgen receptor in a subject, comprising administering to the subject a therapeutically effective amount of crystalline 6-[(4R)-4-methyl-1,1-dioxido-1,2,6-thiadiazinan-2-yl]isoquinoline-1-carbonitrile Form (1), or a pharmaceutical composition thereof.

In yet another aspect, this invention relates to a method for treating a disorder or condition in a subject, wherein the disorder or condition is selected from among anemia; anorexia; arthritis; bone disease; musculoskeletal impairment; cachexia; frailty; age-related functional decline in the elderly; growth hormone deficiency; hematopoietic disorders; hormone replacement; hypogonadism; loss of muscle strength and/or function; muscular dystrophies; muscle loss following surgery; muscular atrophy; neurodegenerative disease; neuromuscular disease; obesity; osteoporosis; sarcopenia, including sarcopenia in chronic obstructive pulmonary disease; and, muscle wasting comprising administering to said subject an effective amount of a crystalline form of 6-[(4R)-4-methyl-1,1-dioxido-1,2,6-thiadiazinan-2-yl]isoquinoline-1-carbonitrile, or a pharmaceutical composition thereof, thereby treating said disease or condition.

In yet another aspect, this invention relates to a method for treating a disorder or condition in a subject, wherein the disorder or condition is selected from among anemia; anorexia; arthritis; bone disease; musculoskeletal impairment; cachexia; frailty; age-related functional decline in the elderly; growth hormone deficiency; hematopoietic disorders; hormone replacement; hypogonadism; loss of muscle strength and/or function; muscular dystrophies; muscle loss following surgery; muscular atrophy; neurodegenerative disease; neuromuscular disease; obesity; osteoporosis; sarcopenia, including sarcopenia in chronic obstructive pulmonary disease; and, muscle wasting comprising administering to said subject an effective amount of crystalline 6-[(4R)-4-methyl-1,1-dioxido-1,2,6-thiadiazinan-2-yl]isoquinoline-1-carbonitrile Form (1), or a pharmaceutical composition thereof, thereby treating said disease or condition.

This invention also relates to a crystalline form of 6-[(4R)-4-methyl-1,1-dioxido-1,2,6-thiadiazinan-2-yl]isoquinoline-1-carbonitrile, or a pharmaceutical composition thereof, for use as a medicament.

This invention also relates to crystalline 6-[(4R)-4-methyl-1,1-dioxido-1,2,6-thiadiazinan-2-yl]isoquinoline-1-carbonitrile Form (1), or a pharmaceutical composition thereof, for use as a medicament.

This invention also relates to a crystalline form of 6-[(4R)-4-methyl-1,1-dioxido-1,2,6-thiadiazinan-2-yl]isoquinoline-1-carbonitrile, or a pharmaceutical composition thereof, for use in the treatment of a disorder or condition relating to dysregulation of an androgen receptor.

This invention also relates to crystalline 6-[(4R)-4-methyl-1,1-dioxido-1,2,6-thiadiazinan-2-yl]isoquinoline-1-carbonitrile Form (1), or a pharmaceutical composition thereof, for use in the treatment of a disorder or condition relating to dysregulation of an androgen receptor.

This invention also relates to a crystalline form of 6-[(4R)-4-methyl-1,1-dioxido-1,2,6-thiadiazinan-2-yl]isoquinoline-1-carbonitrile, or a pharmaceutical composition thereof, for use in the treatment of a disorder or condition selected from the group consisting of anemia; anorexia; arthritis; bone disease; musculoskeletal impairment; cachexia; frailty; age-related functional decline in the elderly; growth hormone deficiency; hematopoietic disorders; hormone replacement; hypogonadism; loss of muscle strength and/or function; muscular dystrophies; muscle loss following surgery; muscular atrophy; neurodegenerative disease; neuromuscular disease; obesity; osteoporosis; sarcopenia, including sarcopenia in chronic obstructive pulmonary disease; and, muscle wasting.

This invention also relates to crystalline 6-[(4R)-4-methyl-1,1-dioxido-1,2,6-thiadiazinan-2-yl]isoquinoline-1-carbonitrile Form (1), or a pharmaceutical composition thereof, for use in the treatment of a disorder or condition selected from the group consisting of anemia; anorexia; arthritis; bone disease; musculoskeletal impairment; cachexia; frailty; age-related functional decline in the elderly; growth hormone deficiency; hematopoietic disorders; hormone replacement; hypogonadism; loss of muscle strength and/or function; muscular dystrophies; muscle loss following surgery; muscular atrophy; neurodegenerative disease; neuromuscular disease; obesity; osteoporosis; sarcopenia, including sarcopenia in chronic obstructive pulmonary disease; and, muscle wasting.

This invention also relates to the use of a crystalline form of 6-[(4R)-4-methyl-1,1-dioxido-1,2,6-thiadiazinan-2-yl]isoquinoline-1-carbonitrile, or a pharmaceutical composition thereof, for the manufacture of a medicament for the treatment of a disorder or condition relating to dysregulation of an androgen receptor.

This invention also relates to the use of crystalline 6-[(4R)-4-methyl-1,1-dioxido-1,2,6-thiadiazinan-2-yl]isoquinoline-1-carbonitrile Form (1), or a pharmaceutical composition thereof, for the manufacture of a medicament for the treatment of a disorder or condition relating to dysregulation of an androgen receptor.

This invention also relates to the use of a crystalline form of 6-[(4R)-4-methyl-1,1-dioxido-1,2,6-thiadiazinan-2-yl]isoquinoline-1-carbonitrile, or a pharmaceutical composition thereof, for the manufacture of a medicament for the treatment of a disorder or condition selected from the group consisting of anemia; anorexia; arthritis; bone disease; musculoskeletal impairment; cachexia; frailty; age-related functional decline in the elderly; growth hormone deficiency; hematopoietic disorders; hormone replacement; hypogonadism; loss of muscle strength and/or function; muscular dystrophies; muscle loss following surgery; muscular atrophy; neurodegenerative disease; neuromuscular disease; obesity; osteoporosis; sarcopenia, including sarcopenia in chronic obstructive pulmonary disease; and, muscle wasting.

This invention also relates to the use of crystalline 6-[(4R)-4-methyl-1,1-dioxido-1,2,6-thiadiazinan-2-yl]isoquinoline-1-carbonitrile Form (1), or a pharmaceutical composition thereof, for the manufacture of a medicament for the treatment of a disorder or condition selected from the group consisting of anemia; anorexia; arthritis; bone disease; musculoskeletal impairment; cachexia; frailty; age-related functional decline in the elderly; growth hormone deficiency; hematopoietic disorders; hormone replacement; hypogonadism; loss of muscle strength and/or function; muscular dystrophies; muscle loss following surgery; muscular atrophy; neurodegenerative disease; neuromuscular disease; obesity; osteoporosis; sarcopenia, including sarcopenia in chronic obstructive pulmonary disease; and, muscle wasting.

This invention also relates to a pharmaceutical composition comprising a crystalline form of 6-[(4R)-4-methyl-1,1-dioxido-1,2,6-thiadiazinan-2-yl]isoquinoline-1-carbonitrile for treating a disorder or condition relating to dysregulation of an androgen receptor.

This invention also relates to a pharmaceutical composition comprising crystalline 6-[(4R)-4-methyl-1,1-dioxido-1,2,6-thiadiazinan-2-yl]isoquinoline-1-carbonitrile Form (1) for treating a disorder or condition relating to dysregulation of an androgen receptor.

This invention also relates to a pharmaceutical composition comprising a crystalline form of 6-[(4R)-4-methyl-1,1-dioxido-1,2,6-thiadiazinan-2-yl]isoquinoline-1-carbonitrile for treating a disorder or condition selected from the group consisting of anemia; anorexia; arthritis; bone disease; musculoskeletal impairment; cachexia; frailty; age-related functional decline in the elderly; growth hormone deficiency; hematopoietic disorders; hormone replacement; hypogonadism; loss of muscle strength and/or function; muscular dystrophies; muscle loss following surgery; muscular atrophy; neurodegenerative disease; neuromuscular disease; obesity; osteoporosis; sarcopenia, including sarcopenia in chronic obstructive pulmonary disease; and, muscle wasting.

This invention also relates to a pharmaceutical composition comprising crystalline 6-[(4R)-4-methyl-1,1-dioxido-1,2,6-thiadiazinan-2-yl]isoquinoline-1-carbonitrile Form (1) for treating a disorder or condition selected from the group consisting of anemia; anorexia; arthritis; bone disease; musculoskeletal impairment; cachexia; frailty; age-related functional decline in the elderly; growth hormone deficiency; hematopoietic disorders; hormone replacement; hypogonadism; loss of muscle strength and/or function; muscular dystrophies; muscle loss following surgery; muscular atrophy; neurodegenerative disease; neuromuscular disease; obesity; osteoporosis; sarcopenia, including sarcopenia in chronic obstructive pulmonary disease; and, muscle wasting.

As used herein the term "therapeutically effective" is intended to qualify the amount of compound or pharmaceutical compositions, or the combined amount of active ingredients in the case of combination therapy. This amount, or combined amount, will achieve the goal of treating the relevant condition.

As used herein the term "treat," "treatment" or "treating" shall be taken to mean administration of the compound, pharmaceutical composition or combination to effect preventative, palliative, supportive, restorative or curative treatment. The term "treatment" encompasses any objective or subjective improvement in a subject with the relevant condition or disease.

As used herein the term "preventative treatment" shall be taken to mean that the compound, pharmaceutical composition or combination is administered to a subject to inhibit or stop the relevant condition from occurring in a subject, particularly in a subject or member of a population that is significantly predisposed to the relevant condition.

For administration to human patients, the total daily dose of the crystalline form of 6-[(4R)-4-methyl-1,1-dioxido-1,2,6-thiadiazinan-2-yl]isoquinoline-1-carbonitrile is typically in the range of from about 0.01 mg to about 500 mg depending, of course, on the mode of administration and other parameters which are well known, and which can be readily determined using standard methods, to one of ordinary skill in the art. In another embodiment of the present invention, the total daily dose is in the range of from about 0.1 mg to about 300 mg. The total daily dose may be administered in single or divided doses and may, at the physician's discretion, fall outside of the typical range given herein. These dosages are based on an average human subject having a weight of about 65 kg to about 70 kg. The physician will readily be able to determine doses for subjects whose weight falls outside this range such as infants and the elderly.

The crystalline 6-[(4R)-4-methyl-1,1-dioxido-1,2,6-thiadiazinan-2-yl]isoquinoline-1-carbonitrile, or pharmaceutical compositions thereof, of the present invention may also be administered in combination with a second active ingredient. As used herein, the terms "co-administration", "co-administered" and "in combination with", referring to a combination of the crystalline compound of the invention and one or more other therapeutic agents, includes the following:

a. simultaneous administration of such a combination of a compound of the invention and a further therapeutic agent to a patient in need of treatment, when such components are formulated together into a single dosage form which releases said components at substantially the same time to said patient;

b. substantially simultaneous administration of such a combination of a compound of the invention and a further therapeutic agent to a patient in need of treatment, when such components are formulated apart from each other into separate dosage forms which are taken at substantially the same time by said patient, whereupon said components are released at substantially the same time to said patient;

c. sequential administration of such a combination of a compound of the invention and a further therapeutic agent to a patient in need of treatment, when such components are formulated apart from each other into separate dosage forms which are taken at consecutive times by said patient with a significant time interval between each administration, whereupon said components are released at substantially different times to said patient; and, d. sequential administration of such a combination of a compound of the invention and a further therapeutic agent to a patient in need of treatment, when such components are formulated together into a single dosage form which releases said components in a controlled manner.

In as much as it may be desirable to administer a combination of active compounds, for example, for the purpose of treating a particular disease or condition, it is within the scope of the present invention that two or more pharmaceutical compositions, at least one of which contains the crystalline compound of the present invention, may conveniently be combined in the form of a kit suitable for co-administration of the compositions. Thus, a kit of the invention comprises two or more separate pharmaceutical compositions, at least one of which comprises the crystalline form of 6-[(4R)-4-methyl-1,1-dioxido-1,2,6-thiadiazinan-2-yl]isoquinoline-1-carbonitrile of the present invention, and a means for separately retaining said compositions, such as a container, divided bottle, or divided foil packet. An example of such a kit is the familiar blister pack used for the packaging of tablets, capsules and the like. Such a kit is particularly suitable for administering different dosage forms, for example, oral and parenteral, for administering separate compositions at different dosage intervals, or for titrating the separate compositions against one another. To assist compliance, the kit typically comprises directions for administration and may be provided with a so-called memory aid.

The crystalline form of 6-[(4R)-4-methyl-1,1-dioxido-1,2,6-thiadiazinan-2-yl]isoquinoline-1-carbonitrile, or a pharmaceutical composition thereof, of the present invention may also be useful in the field of veterinary medicine. The dosages and dosage forms described hereinabove for human subjects can be adjusted to accommodate the varying size of animals, as is well known to those of ordinary skill in the veterinary art. In another aspect, this invention also provides a method of affecting carcass composition, increasing lean mass, reducing fat mass, reducing percent fat mass, increasing lean:fat, increasing average daily gain (ADG), or decreasing feed to gain ratio (F:G) of an animal, or increasing feed efficiency in an animal, wherein the method comprises administering to the animal an effective amount of a crystalline form of 6-[(4R)-4-methyl-1,1-dioxido-1,2,6-thiadiazinan-2-yl]isoquinoline-1-carbonitrile, or a pharmaceutical composition thereof. In a preferred embodiment, the animal is a cattle or a swine. The phrase "increasing lean mass" generally refers to increasing muscle in an animal, which is considered in many cases a more desirable carcass for human food consumption. "Reducing fat mass" and "reducing percent fat mass" refer to reduction of fat production in an animal. The phrase "lean:fat", as for example in "increasing lean:fat" refers generally to the ratio of lean mass in an animal relative to fat mass in the animal. An increased lean:fat in an animal is in many cases considered to produce a carcass that is more desirable for human food consumption. The phrase "F:G" refers to the ratio of feed input into an animal relative to weight gain (output) in the animal. A decrease in F:G increases productivity from an economic view point. Dosage forms, the effective amount of active ingredient and suitable compositions will be known to those of ordinary skill can be used for such veterinary applications.

The crystalline form of 6-[(4R)-4-methyl-1,1-dioxido-1,2,6-thiadiazinan-2-yl]isoquinoline-1-carbonitrile, or a pharmaceutical composition thereof, of the present invention may also be usefully combined with other active pharmaceutical ingredients known in the veterinary fields. Such combinations may be accomplished by administering a compound of the present invention to an animal, as described herein, in one dosage form or unit, and administering the second active pharmaceutical ingredient to the animal separately, in a separate dosage form or unit. The administration to the animal of the two separate dosage forms may be at the same time or in any order. In another embodiment, the compound of the present invention and the second pharmaceutical ingredient (or additional pharmaceutical ingredients) are combined together in the same dosage form and are administered to the animal together. Examples of compounds which can be suitably administered with the crystalline compounds of the present invention for veterinary applications include beta adrenergic agonist or beta adrenergic modulator, antibiotics or steroids.

All publications (including accession numbers, websites and the like), patents, and patent applications cited herein are hereby incorporated by reference in their entirety for all purposes to the same extent as if individually denoted.

EXAMPLES

The following non limiting Examples further illustrate the present invention.

Unless otherwise stated, all starting materials and reagents are commercially available.

Powder X-Ray Diffraction

Powder X-ray diffraction analysis was conducted using a Bruker AXS D8 ADVANCE diffractometer equipped with a Cu radiation source (K-α average). The system is equipped with a Gobel Mirror and 2.5 axial Soller slits on the primary side. The secondary side utilizes 2.5 axial Soller slits and motorized slits. Diffracted radiation was detected by a Lynx Eye XE detector. The X-ray tube voltage and amperage were set to 40 kV and 40 mA respectively. Data was collected in the Theta-2-Theta configuration with a Cu K-alpha (average) wavelength source scanning from 3.0 to 40.0 degrees 2-Theta using a step size of 0.03 degrees and a step time of 1.0 seconds, at ambient temperature. Samples were prepared by placing them in a silicon low background holder and rotated during collection. Data were collected using Bruker DIFFRAC Plus software (Version 2.0) and analysis was performed by EVA diffract plus software (Version 3.1).

PXRD data file was not processed prior to peak searching. Using the peak search algorithm in the EVA diffract plus software (Version 3.1), peaks were selected with a threshold value of 1 and a width value of 0.3 were used to make preliminary peak assignments. The output of automated assignments was visually checked to ensure validity and adjustments manually made if necessary, in accordance with the routine practice of one of ordinary skill. Peaks with relative intensity of ≥10% were generally chosen. The peaks which were not resolved or were consistent with noise were also discarded. A typical error associated with the peak position from PXRD is +/−0.2° 2-theta.

As used herein the terms "PXRD" and "x-ray powder diffraction pattern" are considered interchangeable and synonymous with the term "powder X-ray diffraction pattern".

Fourier Transform Raman (FT-Raman)

FT-Raman spectra analysis was conducted using a Nicolet NXR FT-Raman accessory attached to the FT-IR bench. The spectrometer was equipped with a 1064 nm Nd:YVO$_4$ laser and a liquid nitrogen cooled Germanium detector. Prior to data acquisition, instrument performance and calibration verifications were conducted using polystyrene. Samples were analyzed in glass NMR tubes that were spun during spectral collection. The spectra were collected using 0.5 W of laser power and 512 co-added scans. The collection range was 3700-50 cm$^{-1}$. The API spectra were recorded using 2 cm$^{-1}$ resolution, and Happ-Genzel apodization was utilized for all of the spectra. A typical error associated with the FT-Raman peak shift is ±2 cm$^{-1}$. It is expected that, due to the similarity of FT-Raman and dispersive Raman spectra techniques, peak positions reported herein obtained using FT-Raman spectroscopy would be likely to be consistent with those which would be observed using dispersive Raman spectroscopy assuming appropriate instrument calibration.

Solid State NMR

Solid State NMR (ssNMR) spectra analysis was conducted at 25° C. on a Varian 4 mm CPMAS probe positioned into a Varian VNMR 400 MHz (1H frequency) NMR spectrometer. The sample was packed into a rotor and the rotor was oriented at the magic angle and spun at 8.0 kHz. The carbon ssNMR spectrum was collected using a proton decoupled cross-polarization magic angle spinning (CP-MAS) experiment with TOSS (Total suppression of spinning sidebands) spinning sideband suppression. The cross-polarization contact time was set to 3 ms and the recycle delay to 30 seconds. The carbon spectrum was referenced using an external standard of crystalline adamantane, setting its downfield resonance to 38.5 ppm (as determined from neat TMS).

The ssNMR data file was processed prior to peak searching. Automatic peak picking was performed using Bruker-BioSpin TopSpin software (Version 3.1). Generally, a threshold value of 5% relative intensity was used for peak selection. A typical error associated with the $^{13}$C chemical shift (ppm) x-axis value for ssNMR is ±0.2 ppm.

DSC

DSC measurements were performed with a Discovery DSC (TA instruments) equipped with a refrigerated cooling accessory. Approximately 2-5 mg of solid sample was weighed into a standard/Tzero aluminum pan and non-hermetically sealed. The sample was placed in a cell with continuous dry nitrogen purge (50 mL/min) and heated from 25° C. to 250° C. at 10° C./min heating rate. The cell constant was determined using indium and temperature calibration was performed using indium and tin as standards. The experimental data were analyzed using commercially available software (TA Universal Analysis 2000/Trios software, TA Instruments).

Example 1

Procedure:

Into a 2 L 3-neck round bottom flask equipped with a mechanical stirrer, reflux condenser and thermocouple with heating mantle was placed 2-methyltetrahydrofuran (2-MeTHF) (10 mL/g; 8.15 moles; 817 mL; 702 g) followed by racemic-2,2'-bis(diphenylphosphino)-1,1'-binaphthyl (BINAP) (0.04 equiv (molar); 14.0 mmol; 8.74 g) and bis(dibenzylideneacetone)palladium (Pd$_2$(dba)$_3$) (0.04 equiv (molar); 14.0 mmol; 8.07 g). The mixture was degassed by pulling vacuum and refilling with nitrogen three times then heated to 75° C. for 15 minutes and cooled to ambient temperature. In a separate flask, (S)-3-amino-2-methylpropan-1-ol (1.60 equiv; 561 mmol; 50.0 g, prepared using literature methods, for example as disclosed in EP-A-0,089,139 published on 21 Sep. 1983) was dissolved in 2-methyltetrahydrofuran (5 mL/g; 4.08 moles; 409 mL; 351 g) and degassed by pulling vacuum and refilling with nitrogen three times. Into the pot containing the catalyst was added 6-(bromoisoquinoline-1-carbonitrile) (1.00 equiv; 351 mmol; 81.75 g) and cesium carbonate (1.6 equiv (molar); 561 mmol; 185 g) in single portions followed by the solution of the aminoalcohol via addition funnel. The reaction mixture was again degassed by pulling vacuum and refilling with nitrogen three times. The reaction was heated to 70° C. for 3 hours. The reaction was cooled to ambient temperature and filtered through a pad of Celite. The contents of the flask were rinsed out with three 100 mL portions of 2-methyltetrahydrofuran. The filtrate was transferred into a 2 L round bottom flask equipped with a thermocouple and mechanical stirrer under nitrogen. Silica Gel (Silicylate SiliaMet® Thiol) (0.4 g/g-pure-LR; 544 mmol; 32.7 g) was charged and the flask was stirred at 40° C. overnight. The following morning, the reaction was cooled to <30° C. and filtered again through Celite. The pad was washed with 100 mL of 2-methyltetrahydrofuran (or until no yellow color persisted in the filtrate). The filtrate was placed into a 3 L round bottom flask equipped with a magnetic stir bar, distillation head (with condenser and receiving flask), and thermocouple. The mixture was heated to 60° C. and placed under vacuum (~450-500 mbar) to distil out 1.3 L total of 2-methyltetrahydrofuran. 500 mL of toluene was added to precipitate the desired product. The heating mantle was removed and the reaction was allowed to reach ambient temperature. The mixture was stirred for 1 hour at ambient temperature and then the solids were collected by vacuum filtration on a sintered glass funnel. The cake was dried overnight on the funnel under vacuum. The following morning, the solids were transferred into an amber bottle and weighed (71.9 g; 298 mmol). The product was used in the next step without further purification.

Example 2

Procedure:

In a 1 L reactor equipped with a temperature probe and overhead stirring was added the product of Example 1 (20.0 g; 1.00 equiv; 82.9 mmol) and 2-methyltetrahydrofuran (2-MeTHF) (30 mL/g-pure-LR, 5.98 moles; 600 mL; 515 g). The reaction mixture was gently warmed to 40° C. to achieve partial solubility. The reaction was cooled to 0° C. Once the reaction reached 0° C. methanesulfonyl chloride (MsCl) (1.4 equiv (molar); 116 mmol; 8.98 mL; 13.3 g) was added in a single portion followed immediately by triethylamine (TEA) (1.4 equiv (molar); 116 mmol; 16.2 mL; 11.7 g) dropwise via syringe over a period of 15 minutes. The reaction mixture was further stirred for 30 min at 0° C. and then warmed to 23° C. for 60 minutes. The product (26.47 g; 1.00 equiv; 82.88 mmol; 26.47 g; 100% assumed yield) was then used without purification for the sulfonylation reaction.

Example 3

Procedure:

To a solution of t-butyl alcohol (t-BuOH) (1 equiv (molar); 116 mmol; 11.0 mL; 8.60 g) in 2-methyltetrahydrofuran (2-MeTHF) (1 M; 1.16 moles; 116 mL; 99.6 g) at 0° C. was added chlorosulfonyl isocyanate (116 mmol; 1.00 equiv; 10.1 mL; 16.4 g) dropwise. The homogeneous solution was stirred for 30 minutes at ambient temperature and then used directly in the sulfonylation reaction.

Example 4

Sulfonylation Reaction Procedure:

A previously prepared solution of the product of Example 3 (1.4 equiv (molar); 116 mmol; 116 g) in 2-methyltetrahydrofuran was added to a suspension of the product of Example 2 (1.00 equiv; 82.89 mmol; 26.5 g) at 0° C. The mixture was warmed to ambient temperature over 30 minutes. HPLC analysis revealed the reaction was complete. The reaction was quenched with a 10% sodium carbonate solution (2 equiv (molar); 165 mmol; 101 mL; 117 g) and water (to dissolve salts) (5 L/kg; 7.35 moles; 132 mL; 132 g). The top organic layer was removed and passed through a plug of Carbon (Darco G60) (0.5 g/g) on a filter. A significant improvement in color (dark orange to yellow) was observed. The solution was concentrated to 10 total volumes and used in the next step without purification.

Example 5

Procedure:

A solution of the product of Example 4 (1.00 equiv, 82.9 mmol; 41.3 g) in 2-methyltetrahydrofuran (2-MeTHF) (10 mL/g, 4.12 moles; 413 mL; 355 g) was placed into a 1 L reactor equipped with an overhead stirrer and temperature probe. Next, potassium carbonate ($K_2CO_3$) (325 mesh) (6 equiv (molar); 497 mmol; 69.4 g) and water (0.0 L/100-g-bulk-LR; 459 mmol; 8.26 mL; 8.26 g) were added and the mixture heated to 40° C. (jacket temperature) and stirred overnight. The reaction was cooled to ambient temperature and water (4 L/kg-pure-LR; 9.17 moles; 165 mL; 165 g]) was added. The biphasic reaction was stirred for 1 hour at 23° C. The aqueous layer was extracted and removed. The organic layer was passed through a plug of Carbon (Darco G60) (0.5 g/g-pure-LR; 20.7 g) in a disposable filter. The 2-methyltetrahydrofuran solution was switched to a 10 volume solution of toluene via a constant strip-and-replace distillation to no more than 1% 2-methyltetrahydrofuran. The toluene solution of the reaction product (1.00 equiv; 82.9 mmol; 33.4 g; 100% assumed yield) was used as-is in the next step without further purification.

Example 6

Procedure:

To a 1 L reactor under nitrogen and equipped with overhead stirring and a temperature probe was added the product of Example 5 (1.00 equiv; 78.7 mmol; 33.4 g) as a solution in toluene (10 mL/g-pure-LR, 3.00 moles; 317 mL; 276 g). Next, trifluoroacetic acid (TFA) (10 equiv (molar); 787 mmol; 59.5 mL; 89.8 g) was added to the reaction over a period of 1 hour keeping the internal temperature below 30° C. The dark red mixture was stirred for 1 hour. The reaction was quenched at 23° C. by the addition of sodium carbonate (5 equiv (molar); 394 mmol; 240 mL; 278 g). The reaction was quenched slowly, over a period of 1 hour to form the TFA salt of the product. Once the charge was complete, the mixture was cooled to 0° C., held for 1 hour and filtered. The next morning, the solid product (6-[(4R)-4-methyl-1,1-dioxido-1,2,6-thiadiazinan-2-yl]isoquinoline-1-carbonitrile in its free base form) was weighed (0.89 equiv; 70.0 mmol; 21.2 g; 89.0% yield) and used in the next step without further purification.

Example 7

Crystalline 6-[(4R)-4-methyl-1,1-dioxido-1,2,6-thiadiazinan-2-yl]isoquinoline-1-carbonitrile free base (Form (1)) was prepared as follows.

In a 1 L 3-neck round bottom flask was added 6-[(4R)-4-methyl-1,1-dioxido-1,2,6-thiadiazinan-2-yl]isoquinoline-1-carbonitrile free base (1.00 equiv; 70.0 mmol; 21.2 g) a magnetic stir bar and acetone (40 mL/g, 11.5 moles; 847 mL; 669 g). The mixture was heated to reflux (approximately 57° C.) and stirred for 1 hour. The mixture was concentrated by atmospheric distillation (heating mantle set at 65° C.) and 40 mL of acetone was collected into a graduated cylinder. Next, water (25 mL/g; 29.4 moles; 530 mL; 530 g) was charged over a period of one hour. The mixture was stirred at ambient temperature for 60 min before being cooled to 0° C. at 1° C./min for 1 hour. The solids were collected by filtration in a disposable funnel. Crystalline 6-[(4R)-4-methyl-1,1-dioxido-1,2,6-thiadiazinan-2-yl]isoquinoline-1-carbonitrile (Form (1), 0.88 equiv; 61.9 mmol; 18.7 g; 88.3% yield) was dried under vacuum overnight at 40° C. Typical purity after crystallization is 98%.

Example 8

Figure 1:
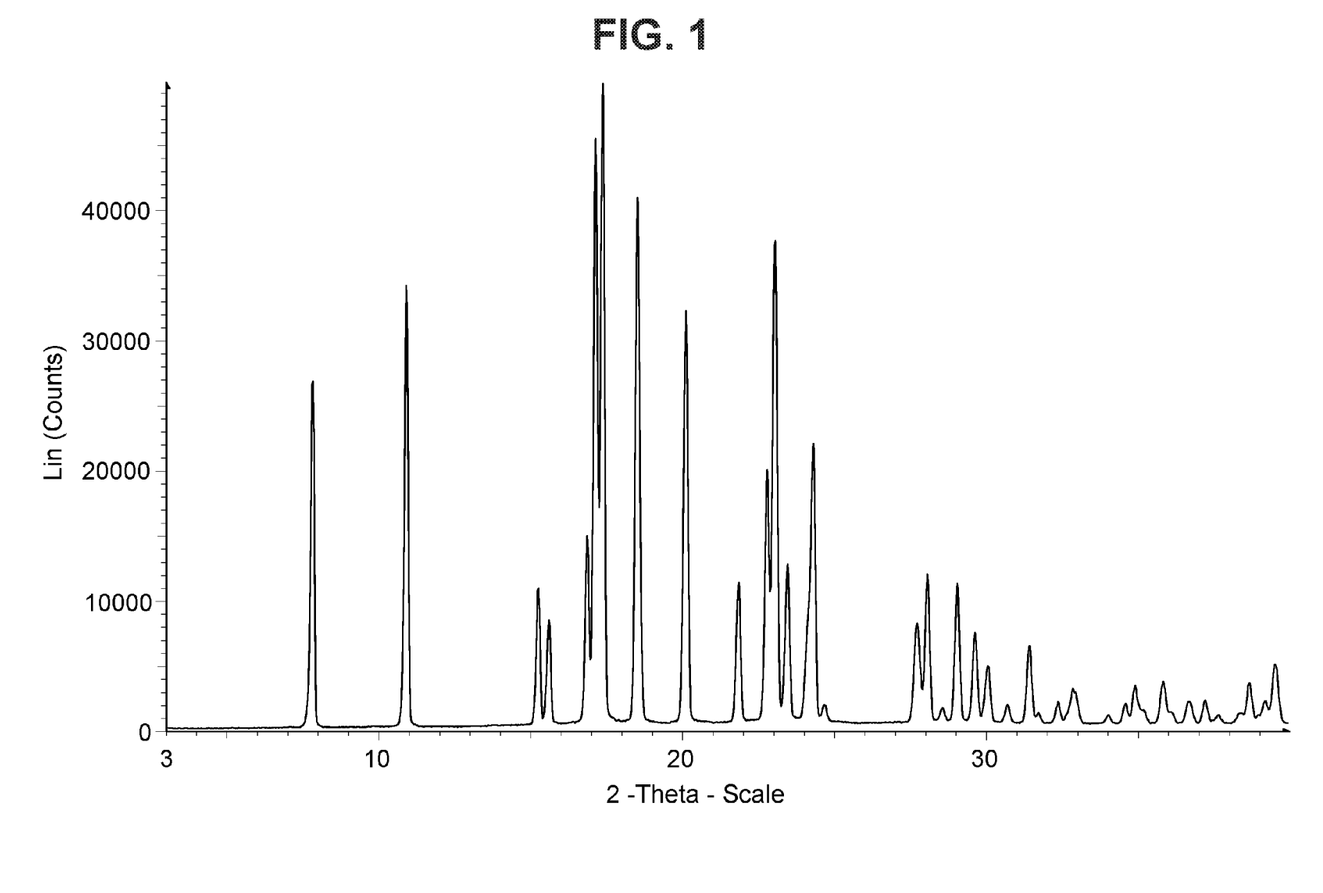
FIG. 1 is a characteristic PXRD pattern of crystalline 6-[(4R)-4-methyl-1,1-dioxido-1,2,6-thiadiazinan-2-yl]isoquinoline-1-carbonitrile free base (Form (1)). (Vertical axis—intensity (counts); horizontal axis: 2-theta (degrees)).

The powder X-ray diffraction pattern of crystalline 6-[(4R)-4-methyl-1,1-dioxido-1,2,6-thiadiazinan-2-yl]isoquinoline-1-carbonitrile was collected using a Bruker AXS D8 ADVANCE diffractometer equipped with a Cu radiation source and then processed as set out above. The results are shown in FIG. 1 and are summarised in Table 1 below.

TABLE 1

PXRD Peak list for crystalline 6-[(4R)-4-methyl-1,1-dioxido-1,2,6-thiadiazinan-2-yl]isoquinoline-1-carbonitrile free base (Form (1))

| Angle degrees 2-Theta (±0.2° 2-theta) | Intensity %* |
|---|---|
| 7.8 | 54 |
| 10.9 | 69 |
| 15.2 | 22 |
| 15.6 | 17 |
| 16.8 | 30 |
| 17.1 | 92 |
| 17.3 | 100 |
| 18.5 | 82 |

TABLE 1-continued

PXRD Peak list for crystalline 6-[(4R)-4-methyl-1,1-dioxido-1,2,6-thiadiazinan-2-yl]isoquinoline-1-carbonitrile free base (Form (1))

| Angle degrees 2-Theta (±0.2° 2-theta) | Intensity %* |
|---|---|
| 20.1 | 65 |
| 21.8 | 23 |
| 22.8 | 40 |
| 23.0 | 76 |
| 23.4 | 26 |
| 24.3 | 44 |
| 27.7 | 17 |
| 28.1 | 24 |
| 29.0 | 23 |
| 29.6 | 15 |
| 30.0 | 10 |
| 31.4 | 13 |
| 39.5 | 10 |

*Relative intensities may vary depending on sample orientation, crystal size and/or morphology.

Example 9

Figure 2:
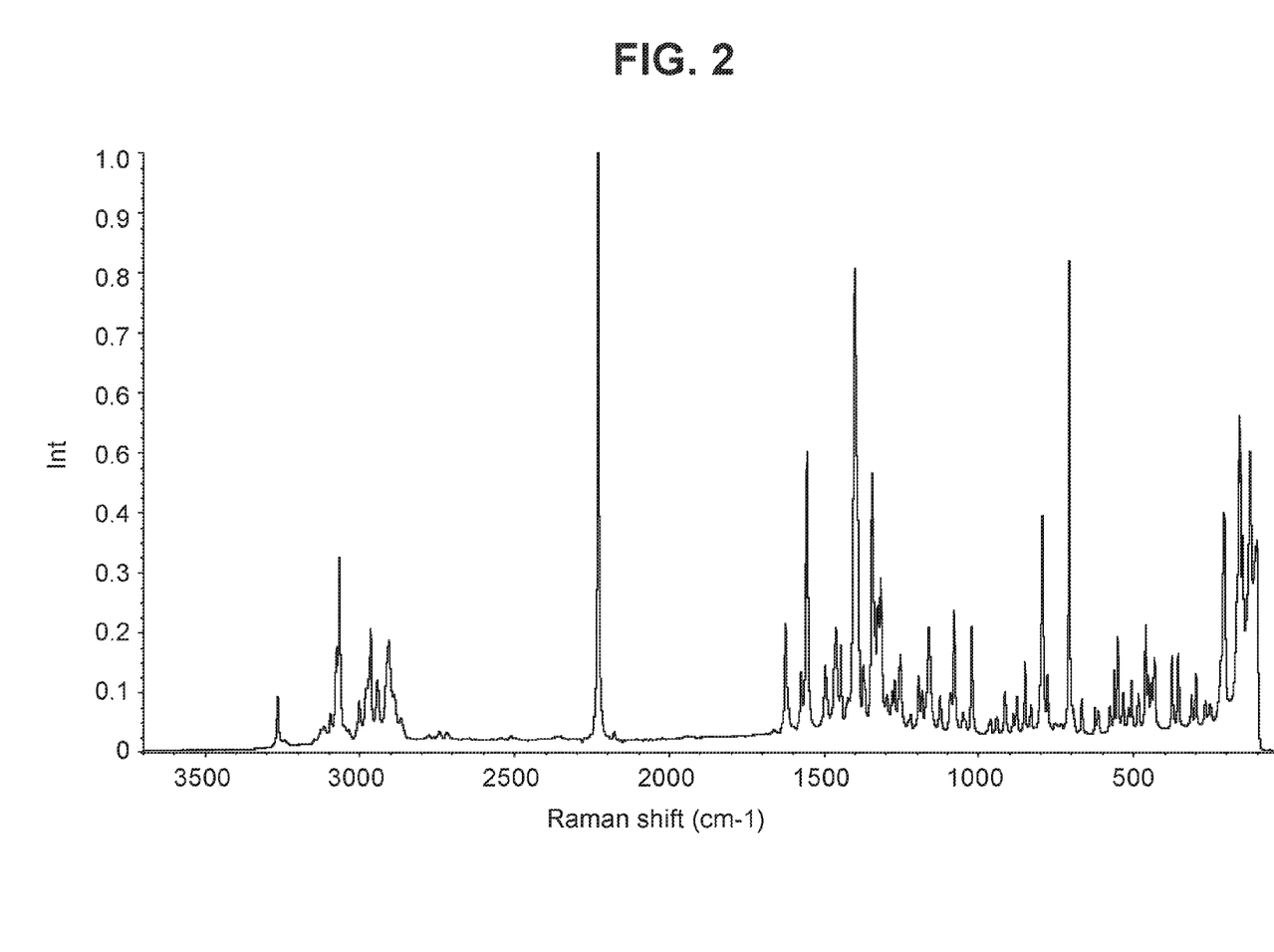
FIG. 2 is a characteristic Raman spectrum of crystalline 6-[(4R)-4-methyl-1,1-dioxido-1,2,6-thiadiazinan-2-yl]isoquinoline-1-carbonitrile free base (Form (1)). (Vertical axis intensity (counts), horizontal axis: Raman shift (cm$^{-1}$)).

The Raman spectra of crystalline 6-[(4R)-4-methyl-1,1-dioxido-1,2,6-thiadiazinan-2-yl]isoquinoline-1-carbonitrile (Form (1)) was collected using a Nicolet NXR FT-Raman accessory attached to the FT-IR bench, equipped with a 1064 nm Nd:YVO$_4$ laser and a liquid nitrogen cooled Germanium detector in accordance with the experimental details and data processing details set out above. The results are shown in FIG. 2 and are summarised in Table 2 below.

TABLE 2

Raman spectra peak list for crystalline 6-[(4R)-4-methyl-1,1-dioxido-1,2,6-thiadiazinan-2-yl]isoquinoline-1-carbonitrile free base (Form (1))

| Position (cm$^{-1}$) | Intensity (W = weak, M = medium, S = strong) |
|---|---|
| 207 | M |
| 667 | W |
| 708 | S |
| 795 | M |
| 1496 | W |
| 1555 | M |
| 1575 | W |
| 1624 | W |
| 2230 | S |
| 3067 | M |
| 3077 | W |
| 3095 | W |
| 3116 | W |
| 3265 | W |

Example 10

Figure 3:
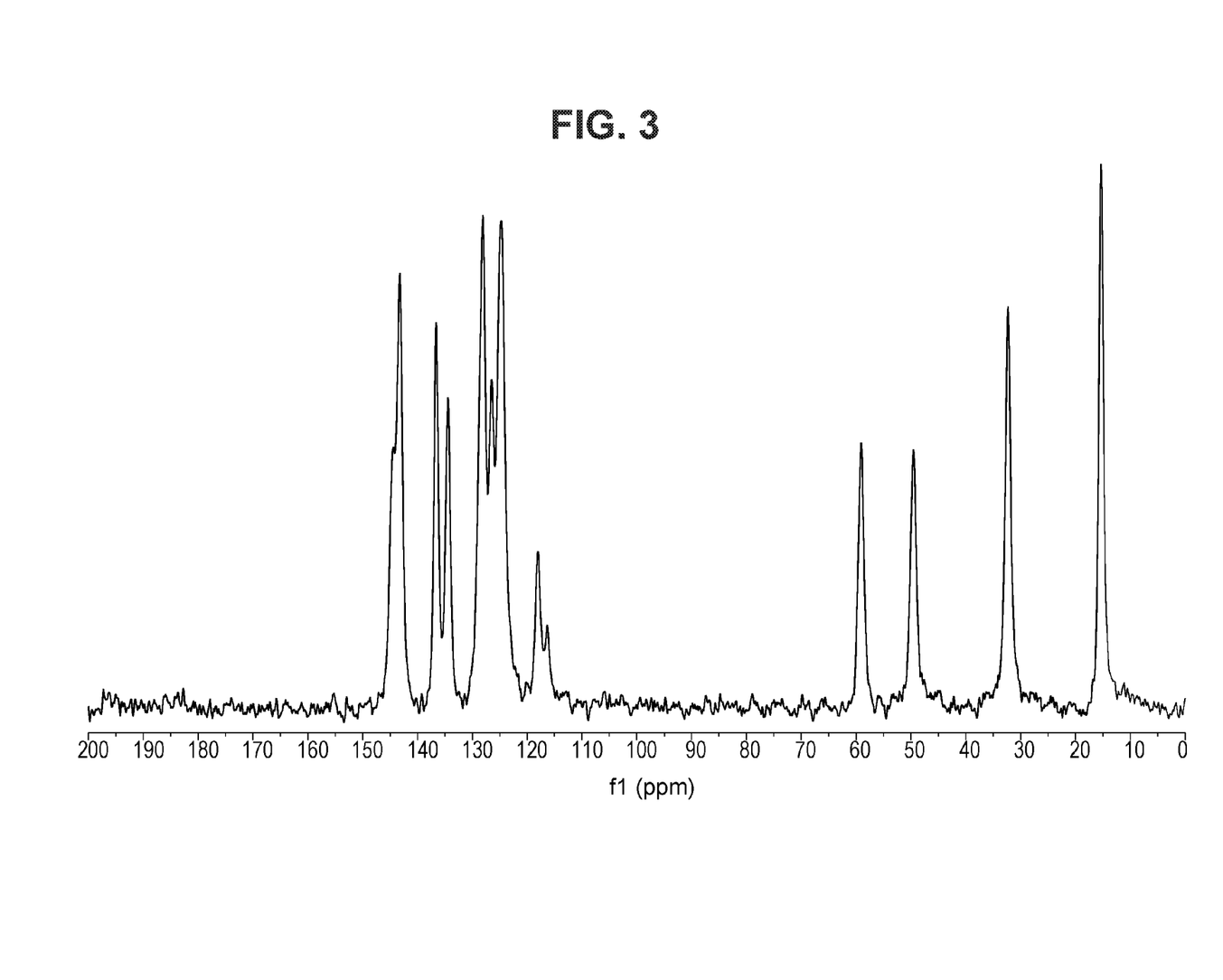
FIG. 3 is a characteristic solid state NMR spectrum of crystalline 6-[(4R)-4-methyl-1,1-dioxido-1,2,6-thiadiazinan-2-yl]isoquinoline-1-carbonitrile free base (Form (1)). (Horizontal axis peak shift (ppm)).

The solid state NMR (ssNMR) spectra of crystalline 6-[(4R)-4-methyl-1,1-dioxido-1,2,6-thiadiazinan-2-yl]isoquinoline-1-carbonitrile (Form (1)) was collected at 25° C. using a Varian 4 mm CPMAS probe positioned into a Varian VNMR 400 MHz (1H frequency) NMR spectrometer in accordance with the experimental details and data processing details set out above. The results are shown in FIG. 3 and are summarised in Table 3 below.

TABLE 3

Solid state NMR (ssNMR) peak list for crystalline
6-[(4R)-4-methyl-1,1-dioxido-1,2,6-thiadiazinan-
2-yl]isoquinoline-1-carbonitrile free base (Form (1))
$^{13}$C Chemical Shifts
[ppm]

15.3
32.3
49.6
59.1
116.4
118.0
124.7
124.9
126.5
128.1
128.6
134.4
136.6
143.2
144.4

Example 11—Immediate Release Tablet

An immediate release tablet formulation comprising crystalline 6-[(4R)-4-methyl-1,1-dioxido-1,2,6-thiadiazinan-2-yl]isoquinoline-1-carbonitrile (Form (1)) can be prepared as shown. Tablets can be prepared using three different strengths of active ingredient (A).

| Ingredient | Tablet 1 (1 mgA Dose) | | Tablet 2 (5 mgA Dose) | | Tablet 3 (25 mgA Dose) | |
|---|---|---|---|---|---|---|
| | mg/ tablet | % w/w | mg/ tablet | % w/w | mg/ tablet | % w/w |
| Active (SARM)[1] | 1 | 1% | 5 | 5% | 25 | 5% |
| Microcrystalline cellulose, NF [2] | 63.3 | 63% | 60.7 | 61% | 303.5 | 61% |
| Lactose monohydrate, NF[3] | 31.7 | 32% | 30.3 | 30% | 151.5 | 30% |
| Sodium starch glycolate, NF[4] | 3 | 3% | 3 | 3% | 15 | 3% |
| Magnesium stearate, NF[5] | 1 | 1% | 1 | 1% | 5 | 1% |
| Total | 100 | 100% | 100 | 100% | 500 | 100% |

[1]Assumes 100% purity and no salt form. When a potency adjustment is required the amounts of microcrystalline cellulose and lactose monohydrate may be adjusted
[2] Avicel PH102, FMC Corporation
[3]Fast Flo, Foremost Farms
[4]Explotab, Penwest Pharmaceuticals
[5]Vegetable derived; Malinkrodt The tablet formulation may be prepared using direct compression or wet or dry granulation processes. Alternatively, the formulation may be used for filling hard-shell capsules or other dosage forms.

In this case, direct compression can be used to manufacture the tablet and a standard blend-mill-blend process can be used to prepare the blend. For example, first, all of the ingredients except magnesium stearate would be added to a bin. The material would then be mixed until well blended. The material would then be passed through a mill. The material would then be mixed again until well blended. The magnesium stearate would then be added to the mixture and mixed again. Finally, the resulting mixture would then be compressed into a tablet.

Example 12—Immediate Release Tablet Formulation

An immediate release tablet formulation comprising crystalline 6-[(4R)-4-methyl-1,1-dioxido-1,2,6-thiadiazinan-2-yl]isoquinoline-1-carbonitrile (Form (1)) can be prepared as shown. Tablets can be prepared using three different strengths of active ingredient (A).

| Ingredient | Tablet 1 (1 mgA Dose) | | Tablet 2 (5 mgA Dose) | | Tablet 3 (25 mgA Dose) | |
|---|---|---|---|---|---|---|
| | mg/ tablet | % w/w | mg/ tablet | % w/w | mg/ tablet | % w/w |
| Active (SARM)[1] | 1 | 1% | 5 | 5% | 25 | 5% |
| Microcrystalline cellulose, NF[2] | 47.5 | 48% | 45.5 | 46% | 227.5 | 46% |
| Lactose monohydrate, NF[3] | 47.5 | 48% | 45.5 | 46% | 227.5 | 46% |
| Sodium starch glycolate, NF[4] | 3 | 3% | 3 | 3% | 15 | 3% |
| Magnesium stearate, NF[5] | 1 | 1% | 1 | 1% | 5 | 1% |
| Total | 100 | 100% | 100 | 100% | 500 | 100% |

[1]Assumes 100% purity and no salt form. When a potency adjustment is required the amounts of microcrystalline cellulose and lactose monohydrate may be adjusted
[2]Avicel PH102, FMC Corporation
[3]Fast Flo, Foremost Farms
[4]Explotab, Penwest Pharmaceuticals
[5]Vegetable derived; Malinkrodt Tablets containing the ingredients shown can be prepared by the direct compression method described in Example 11. Alternatively, the formulation may be used for filling hard-shell capsules or tableted using a wet or dry granulation process.

Example 13—Immediate Release Tablet Formulation

An immediate release tablet formulation comprising crystalline 6-[(4R)-4-methyl-1,1-dioxido-1,2,6-thiadiazinan-2-yl]isoquinoline-1-carbonitrile (Form (1)) can be prepared as shown. Tablets can be prepared using three different strengths of active ingredient (A).

| Ingredient | Tablet 1 (1 mgA Dose) | | Tablet 2 (5 mgA Dose) | | Tablet 3 (25 mgA Dose) | |
|---|---|---|---|---|---|---|
| | mg/ tablet | % w/w | mg/ tablet | % w/w | mg/ tablet | % w/w |
| Active (SARM)[1] | 1 | 1% | 5 | 5% | 25 | 5% |
| Microcrystalline cellulose, NF[2] | 63.3 | 63% | 60.7 | 61% | 303.5 | 61% |
| Calcium phosphate, dibasic anhydrous[3] | 31.7 | 32% | 30.3 | 30% | 151.5 | 30% |
| Sodium starch glycolate, NF[4] | 3 | 3% | 3 | 3% | 15 | 3% |
| Magnesium stearate, NF[5] | 1 | 1% | 1 | 1% | 5 | 1% |
| Total | 100 | 100% | 100 | 100% | 500 | 100% |

[1]Assumes 100% purity and no salt form. When a potency adjustment is required the amounts of microcrystalline cellulose and lactose monohydrate may be adjusted
[2]Avicel PH102, FMC Corporation
[3]A-tab, Rhodia Incorporated
[4]Explotab, Penwest Pharmaceuticals
[5]Vegetable derived; Malinkrodt Tablets containing the ingredients shown can be prepared by the direct compression method described in Example 11.

Alternatively, the formulation may be used for filling hard-shell capsules or tableted using a wet or dry granulation process.

Example 14—Immediate Release Tablet Formulation

An immediate release tablet formulation comprising crystalline 6-[(4R)-4-methyl-1,1-dioxido-1,2,6-thiadiazinan-2-yl]isoquinoline-1-carbonitrile (Form (1)) can be prepared as shown. Tablets can be prepared using three different strengths of active ingredient (A).

| Ingredient | Tablet 1 (1 mgA Dose) | | Tablet 2 (5 mgA Dose) | | Tablet 3 (25 mgA Dose) | |
|---|---|---|---|---|---|---|
| | mg/tablet | % w/w | mg/tablet | % w/w | mg/tablet | % w/w |
| Active (SARM)[1] | 1 | 1% | 5 | 5% | 25 | 5% |
| Microcrystalline cellulose, NF[2] | 47.5 | 48% | 45.5 | 46% | 227.5 | 46% |
| Calcium phosphate, dibasic anhydrous[3] | 47.5 | 48% | 45.5 | 46% | 227.5 | 46% |
| Sodium starch glycolate, NF[4] | 3 | 3% | 3 | 3% | 15 | 3% |
| Magnesium stearate, NF[5] | 1 | 1% | 1 | 1% | 5 | 1% |
| Total | 100 | 100% | 100 | 100% | 500 | 100% |

[1] Assumes 100% purity and no salt form. When a potency adjustment is required the amounts of microcrystalline cellulose and lactose monohydrate may be adjusted
[2] Avicel PH102, FMC Corporation
[3] A-tab, Rhodia Incorporated
[4] Explotab, Penwest Pharmaceuticals
[5] Vegetable derived; Malinkrodt Tablets containing the ingredients shown can be prepared by the direct compression method described in Example 11.

Alternatively, the formulation may be used for filling hard-shell capsules or tableted using a wet or dry granulation process.

Figure 4:
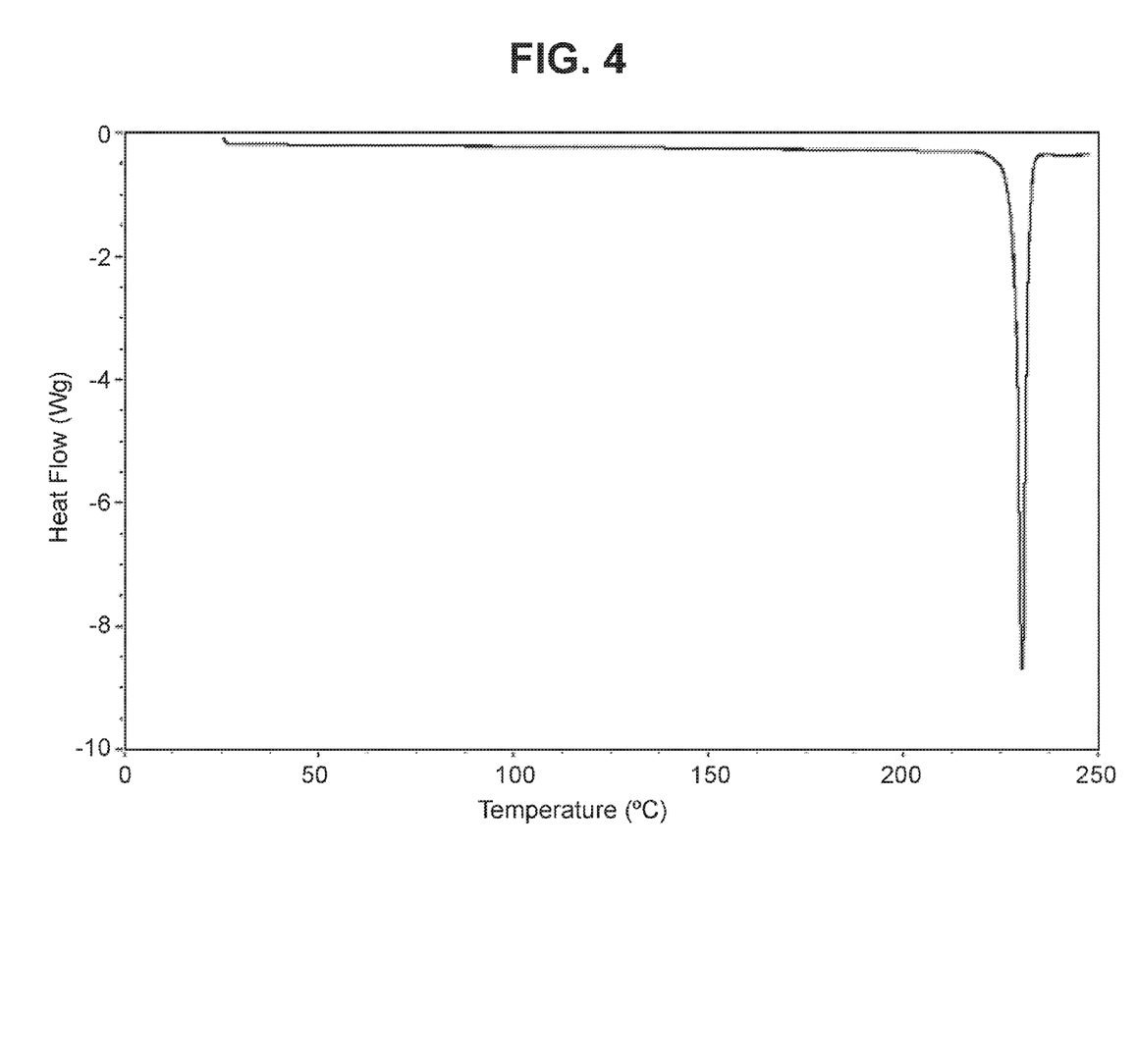
FIG. 4 is a characteristic DSC diffractogram of crystalline 6-[(4R)-4-methyl-1,1-dioxido-1,2,6-thiadiazinan-2-yl]isoquinoline-1-carbonitrile free base (Form (1)). (Vertical axis heat flow (W/g), horizontal axis temperature (° C.)).

The characterization data disclosed herein confirms the crystalline nature of the 6-[(4R)-4-methyl-1,1-dioxido-1,2,6-thiadiazinan-2-yl]isoquinoline-1-carbonitrile free base Form (1) material and, as such, that it is a useful form for pharmaceutical development. For example, crystalline materials are generally considered to be an advantageous form for drug substance manufacturing because, for example, they are more easily purified, can be prepared with higher yields, have improved filtration and drying characteristics and improved flow and handling characteristics. Crystalline 6-[(4R)-4-methyl-1,1-dioxido-1,2,6-thiadiazinan-2-yl]isoquinoline-1-carbonitrile Form (1) also demonstrates physicochemical properties which render it useful for drug product manufacturing such as its thermal stability and non-hygroscopic nature demonstrated by the high DSC melting point and DSC profile.

What is claimed is:

1. A crystalline form of 6-[(4R)-4-methyl-1,1-dioxido-1,2,6-thiadiazinan-2-yl]isoquinoline-1-carbonitrile having an X-ray powder diffraction pattern with characteristic peaks expressed in degrees 2-theta (±0.2° 2-theta) at 7.8, 10.9 and 15.2.

2. A crystalline form of 6-[(4R)-4-methyl-1,1-dioxido-1,2,6-thiadiazinan-2-yl]isoquinoline-1-carbonitrile according to claim 1 having a further-characteristic peak expressed in degrees 2-theta (±0.2° 2-theta) selected from the group consisting of 17.1, 17.3, and 18.5.

3. A crystalline form of 6-[(4R)-4-methyl-1,1-dioxido-1,2,6-thiadiazinan-2-yl]isoquinoline-1-carbonitrile according to claim 1 or 2, which crystalline form is anhydrous.

* * * * *